United States Patent [19]
Barron et al.

[11] Patent Number: 5,990,233
[45] Date of Patent: *Nov. 23, 1999

[54] RHEOLOGY MODIFIERS FOR USE IN AQUEOUS COMPOSITIONS

[75] Inventors: Milagros C. Barron, Hixson; Daniel W. Verstrat, Ooltewah; John M. Wilkerson, III, Hixson, all of Tenn.

[73] Assignee: National Starch and Chemical Investment Holding Corporation, Wilmington, Del.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/698,690

[22] Filed: Aug. 16, 1996

[51] Int. Cl.$^6$ .................. C08K 3/20; C08K 5/05
[52] U.S. Cl. .......... 524/767; 524/547; 524/548; 524/555; 524/560; 524/561; 524/765; 524/766
[58] Field of Search .................. 524/765, 766, 524/767, 547, 548, 555, 560, 561

[56] References Cited

U.S. PATENT DOCUMENTS

| | | | |
|---|---|---|---|
| Re. 33,156 | 1/1990 | Shay et al. ............... | 526/301 |
| 4,012,437 | 3/1977 | Shachat et al. .............. | 260/482 R |
| 4,128,520 | 12/1978 | Barabas et al. ............ | 524/824 |
| 4,616,074 | 10/1986 | Ruffner ................... | 526/318 |
| 4,806,345 | 2/1989 | Bhattacharyya ............ | 424/70 |
| 4,892,916 | 1/1990 | Hawe et al. ............... | 526/304 |
| 5,011,987 | 4/1991 | Barron et al. ............. | 560/221 |
| 5,164,177 | 11/1992 | Bhatt et al. ............... | 424/47 |
| 5,238,992 | 8/1993 | Outubuddin .............. | 524/755 |
| 5,294,692 | 3/1994 | Barron et al. ............. | 526/301 |

FOREIGN PATENT DOCUMENTS

| | | |
|---|---|---|
| 190892 | 8/1986 | European Pat. Off. . |
| 0 329 419 A2 | 8/1989 | European Pat. Off. . |
| 0 398 576 B1 | 11/1990 | European Pat. Off. . |
| 49-5512 | 2/1974 | Japan . |

OTHER PUBLICATIONS

J. A. Wenninger & G. N. McEwen, "International Cosmetic Ingredient Handbook", Third Edition, 1995.
K. G. Srinivasan and D. L. Neumann, "Cationic acrylic latex as paper saturants", Sep. 1986 Tappi Journal, pp. 104–106.
J. A. Wenninger & G. N. McEwen, "International Cosmetic Ingredient Handbook", Sixth Edition, 1995.

*Primary Examiner*—Judy M. Reddick
*Attorney, Agent, or Firm*—John D. Thallemer

[57] ABSTRACT

The present invention relates to acrylate-based rheology modifiers for use in aqueous compositions having pH of less than or equal to 9 and to the rheologically-modified aqueous compositions, which modifiers contain an emulsion which is prepared by single-stage emulsion polymerization of a $C_2$–$C_6$ alkyl ester of acrylic acid and/or a $C_1$–$C_6$ alkyl ester of methacrylic acid, a monomer chosen from a vinyl-substituted heterocyclic compound containing at least one of a nitrogen or sulfur atom, (meth)acrylamide, a mono- or di-($C_1$–$C_4$)alkylamino ($C_1$–$C_4$)alkyl (meth)acrylate, a mono or di-($C_1$–$C_4$)alkylamino ($C_1$–$C_4$)alkyl (meth)acrylamide, and optionally cross-linking monomers and/or associative monomers, in the presence of water, a surfactant, a free-radical initiator and an alcohol selected from $C_2$–$C_{12}$ linear or branched alcohols, ethylene glycol, propylene glycol and glycerol, or mixtures thereof, and essentially in the absence of a polymeric colloidal stabilizer such as polyvinyl alcohol.

9 Claims, No Drawings

RHEOLOGY MODIFIERS FOR USE IN AQUEOUS COMPOSITIONS

FIELD OF THE INVENTION

The present invention is related to acrylate-based, polymeric rheology modifiers used to thicken compositions having pH of less than or equal to 9.

BACKGROUND OF THE INVENTION

Rheology modifiers are used generally to adjust or modify the rheological properties of aqueous compositions. Such properties include, without limitation, viscosity, flow rate, stability to viscosity change over time, and the ability to suspend particles in such aqueous compositions. The particular type of modifier used will depend on the particular aqueous composition to be modified and on the particular end-use of that modified aqueous composition. Examples of conventional rheology modifiers include thickeners such as cellulosic derivatives, polyvinyl alcohol, sodium polyacrylate, and other water-soluble macromolecules, and copolymeric emulsions in which monomers with acid groups have been introduced onto the main chain. Such thickeners are used widely in fiber treatment and adhesives.

It has been reported that when thickeners such as cellulosic derivatives and polyvinyl alcohol are mixed with aqueous emulsions, the thickened emulsion tends to exhibit poor stability to viscosity change over time. The cellulosics are said to result in a substantial decline in viscosity over time. It also has been reported that large quantities of polyvinyl alcohol are required in order to thicken aqueous emulsions. When such thickened aqueous emulsions are used in, for example, adhesives and coatings, the high levels of polyvinyl alcohol result in a loss of adhesive and/or cohesive properties as well as a loss in water resistance in the films formed therefrom.

Another class of rheology modifiers known to thicken aqueous emulsions is one typically referred to as associative modifiers. Such associative modifiers are reported in U.S. Pat. Nos. 4,743,698, 4,600,761, RE 33,156, 4,792,343, 4,384,096, 3,657,175, 5,102,936 and 5,294,692. As noted, these thickeners become effective upon the addition of base, thereby raising the pH of the thickened composition to alkaline, but the thickeners do not thicken aqueous compositions having acidic pH.

Other rheology modifiers which are "activated" by the addition of acid to aqueous compositions which contain the modifiers also have been reported. As reported, emulsions are prepared via free-radical emulsion polymerization utilizing colloidal stabilizers. The emulsions are mixed with the composition to be thickened and then acid is added to the mix, thereby lowering the pH of the system to 6.5 to 0.5. These thickeners are reported to be effective at thickening certain acidic aqueous compositions, but are not effective at thickening aqueous compositions having basic pH.

It would be desirable to develop a rheology modifier which is stable to change in viscosity and phase separation over time, which does not detrimentally affect film properties such as adhesive/cohesive properties and water resistance, and which advantageously may be used to thicken both acidic and basic aqueous compositions.

SUMMARY OF THE INVENTION

The present invention relates to compositions which may be used as rheology modifiers, and particularly as thickeners for aqueous compositions having pH of less than 9. The compositions comprise a stable emulsion of a polymer, wherein the stable emulsion is prepared by single-stage emulsion polymerization of from about 5 to about 80 weight percent of an acrylate monomer (a) selected from the group consisting of a $C_2$–$C_6$ alkyl ester of acrylic acid and a $C_1$–$C_6$ alkyl ester of methacrylic acid, from about 5 to about 80 weight percent of a monomer (b) selected from the group consisting of a vinyl-substituted heterocyclic compound containing at least one of a nitrogen or sulfur atom, (meth) acrylamide, a mono- or di- ($C_1$–$C_4$)alkylamino ($C_1$–$C_4$)alkyl (meth)acrylate, a mono or di-($C_1$–$C_4$)alkylamino ($C_1$–$C_4$) alkyl (meth)acrylamide, 0 to about 2 weight percent of a cross-linking monomer (c); and 0 to about 30 weight percent of an associative monomer (d), all percentages based on the total weight of monomer. The emulsion polymerization is conducted in the presence of water, a first surfactant and, optionally, a second surfactant, wherein said first and second surfactants are selected from the group consisting of anionic, cationic, nonionic, amphoteric and zwitterionic surfactants in amounts effective to emulsify the polymer in the water, a free-radical initiator, and from about 0.5 to about 20 weight percent of an alcohol selected from the group consisting of a $C_2$–$C_{12}$ linear or branched monohydric alcohol and non-polymeric polyhydric alcohols, such as ethylene glycol, propylene glycol and glycerol, based on the total weight of the stable emulsion. The emulsion polymerization is conducted essentially in the absence of a polymeric colloidal stabilizer.

DETAILED DESCRIPTION OF THE INVENTION

The present invention relates to acrylate-based emulsions which have been found to be useful as rheology modifiers for aqueous compositions having pH of less than 9. The emulsions may be used to thicken detergent compositions, drilling fluid additives, saturants for corrugated paper manufacture, hair care products, adhesives, paints, and antistat coatings for paper, for example. The emulsions are stable, meaning that no appreciable phase separation or change in viscosity is noted over time, for example one to five days at standard temperature and pressure, such that the emulsions may not be used to thicken aqueous compositions having pH of less than or equal to 9.

The acrylate monomers (a) are selected from the group consisting of esters prepared from acrylic acid and $C_2$–$C_6$ alcohols, such as ethyl or propyl alcohol, and esters prepared from methacrylic acid and $C_1$–$C_6$ alcohols. (Meth)acrylic acid is used herein to denote both acrylic acid and methacrylic acid. Preferred acrylate monomers comprise $C_2$–$C_6$ alkyl esters of acrylic acid. Even more preferred, the acrylate monomer is ethyl acrylate. From about 5 to about 80 weight percent of the acrylate monomer are used in preparing the composition of the present invention, based on total weight of monomer. Preferably from about 15 to about 70 weight percent of the acrylate monomer are used, based on total weight of monomer. More preferably, from about 40 to about 70 weight percent of the acrylate monomer are used.

Methyl acrylate should not be used in the present invention and is not included within the metes and bounds of this invention, as it has been found to result in emulsions which are unstable with respect to viscosity change over time. It was unexpected that polymers prepared in the absence of a polymeric colloidal stabilizer with ethyl acrylate provided stability to viscosity change over time when compared to polymers prepared in the absence of a polymeric colloidal stabilizer with methyl acrylate, as emulsions prepared with methyl acrylate were found to be unstable to viscosity change.

In addition to the acrylate ester (a), polymerized therewith is a monomer (b) selected from the group consisting of a vinyl-substituted heterocyclic compound containing at least one of a nitrogen or sulfur atom, (meth)acrylamide, a mono- or di- ($C_1$–$C_4$)alkylamino ($C_1$–$C_4$)alkyl (meth)acrylate, a mono or di-($C_1$–$C_4$)alkylamino ($C_1$–$C_4$)alkyl (meth) acrylamide. Exemplary monomers include N,N-dimethylamino ethyl methacrylate, N,N-diethylamino ethyl acrylate, N,N-diethylamino ethyl methacrylate, N-t-butylamino ethyl acrylate, N-t-butylamino ethyl methacrylate, N,N-dimethylamino propyl acrylamide, N.N-dimethylamino propyl methacrylamide, N,N- diethylamino propyl acrylamide and N.N-diethylamino propyl methacrylamide. From about 5 to about 80 weight percent of the monomer are used in preparing the modifiers of the present invention, based on total weight of monomer. Preferably, from about 10 to about 70 weight percent of the monomer are used, based on total weight of monomer. More preferably, from about 20 to about 60 weight percent of the monomer are used.

In addition to the required monomers, monomers which provide cross-linking in the polymer may also be utilized in relatively low amounts, up to about 2 weight percent, based on the total weight of monomer. When used, the cross-linking monomers preferably are used at levels of from about 0.1 to about 1 weight percent, based on total weight of monomer. Cross-linking monomers include multi-vinyl-substituted aromatic monomers, alicyclic monomers selected from the group consisting of cycloparrafins and cycloolefins, di-functional esters of phthalic acid, di-functional esters of methacrylic acid, multi-functional esters of acrylic acid, dienes, trienes, tetraenes, and N-methylene-Bis-acrylamide. Exemplary cross-linking monomers include divinylbenzene, trivinylbenzene, 1,2,4-tricinylcyclohexane, 1,5-hexadiene, 1,5,9-decatriene, 1,9-decadiene, and 1,5-heptadiene, di-allyl phthalate, ethylene glycol dimethacrylate, polyethylene glycol dimethacrylate, penta- and tetra-acrylates, and N-methylene-Bis-acrylamide. The polyethylene glycol dimethacrylates are particularly preferred for thickening in acid aqueous compositions, as they tend to minimize turbidity.

In certain preferred embodiments, an associative monomer may be used to prepare the rheology modifiers, in amounts up to about 30 weight percent, based on total weight of monomer. When used, the associative monomers preferably are used at levels ranging from about 0.1 to about 10 weight percent, based on total weight of monomer. Such monomers include those disclosed in U.S. Pat. Nos. 3,657, 175, 4,384,096, 4,616,074, 4,743,698, 4,792,343, 5,011,978, 5,102,936, 5,294,692, and Re. 33,156, the contents of all which are hereby incorporated herein as if set forth in their entirety. Preferred associative monomers include the urethane reaction products of a monoethylenically unsaturated isocyanate and non-ionic surfactants comprising $C_1$–$C_4$ alkoxy-terminated, block copolymers of 1,2-butylene oxide and 1,2-ethylene oxide, as disclosed in U.S. Pat. No. 5,294, 692 (Barron et al.), an ethylenically unsaturated copolymerizable surfactant monomer obtained by condensing a non-ionic surfactant with methylenesuccinic acid (also known as itaconic acid) as disclosed in U.S. Pat. No. 4,616,074 (Ruffner), a surfactant monomer selected from the urea reaction product of a monoethylenically unsaturated monoisocyanate with a nonionic surfactant having amine functionality as disclosed in U.S. Pat. No. 5,011,978 (Barron et al.), and a nonionic urethane monomer which is the urethane reaction product of a monohydric nonionic surfactant with a monoethylenically unsaturated monoisociante, preferably one lacking ester groups such as alpha, alpha-dimethyl-m-iso-propenyl benzyl isocyanate as disclosed in U.S. Re. 33,156 (Shay et al.). Particularly preferred are the ethylenically unsaturated copolymerizable surfactant monomers obtained by condensing a nonionic surfactant with methylenesuccinic acid. Methods for preparing such monomers are disclosed in detail in the various patents incorporated herein above.

The rheology modifier is prepared by first by forming an emulsion utilizing single-stage emulsion polymerization techniques. Monomer, water, free-radical initiator, surfactant in amounts effective to disperse the polymer in the water upon polymerization of the monomers, and from about 0.5 to about 20 weight percent of an alcohol selected from the group consisting of a $C_2$–$C_{12}$ linear or branched monohydric alcohol and a non-polymeric polyhydric alcohol, such as ethylene glycol, propylene glycol and glycerol, based on total weight of the emulsion, are combined in a polymerization reactor and maintained at a desired temperature and for a period of time which are effective to polymerize the monomers, thereby forming a polymeric emulsion comprising the copolymer of monomers (a) and (b), water, surfactant and alcohol.

The contents of the polymerization vessel preferably are maintained at a temperature and for a period of time effective to cause polymerization of the monomers. Preferably the polymerization reaction is initiated at about 30 degrees Centigrade, with the contents of the polymerization vessel attaining a temperature of about 60 degrees Centigrade. The reaction time will be from about 1 to about 6 hours. One skilled in the art of emulsion polymerization will be able to ascertain readily exactly what conditions of temperature and time are required, as both are well within the knowledge of one skilled in the art Preferably, from about 1 to about 10 weight percent of the alcohol are used and, more preferably, from about 1 to about 5 weight percent of the alcohol are used, based on the total weight of the emulsion. If no alcohol, or an insufficient amounts of the alcohol, is used in preparing the emulsion, the resultant emulsion will not be stable to change in viscosity over time. It is desirable to minimize the level of alcohol used. The maximum amount of alcohol used may be limited practically by factors such as cost, flammability and volatile organic compound environmental concerns. Other than those factors, amounts of alcohol in excess of 20 weight percent conceivably may used.

It is essential that polymeric colloidal stabilizers such as polyvinyl alcohol not be used during preparation of the emulsion via emulsion polymerization in any amount which materially alters the properties of the emulsion, particularly the emulsion stability. Preferably, no polymeric colloidal stabilizer is used during emulsion preparation. It was discovered surprisingly that use of such polymeric colloidal stabilizers results in emulsions which are not stable to changes in viscosity or phase separation over time. Accordingly, the emulsions and rheology modifiers comprising the emulsions essentially are free and more preferably are free of polymeric colloidal stabilizers.

We claim:

1. A composition for use as a rheology modifier in aqueous systems having pH of less than or equal to 9, said composition comprising:

a stable emulsion of a polymer, said emulsion prepared by single-stage emulsion polymerization of monomers consisting of from about 5 to about 80 weight percent of an acrylate monomer (a) selected from the group consisting of a $C_2$–$C_6$ alkyl esters of acrylic acid and a $C_1$–$C_6$ alkyl ester of methacrylic acid, and from about 5 to about 80 weight percent of a monomer (b) selected from the group consisting of a vinyl-substituted heterocyclic compound containing at least one of a nitrogen or sulfur atom, (meth)acrylamide, a mono- or di-($C_1$–$C_4$)alkylamino ($C_1$–$C_4$)alkyl (meth)acrylate, and a mono or di-($C_1$–$C_4$)alkylamino ($C_1$–$C_4$)alkyl (meth)acrylamide, wherein the percentage of monomers is based on 100 weight percent, wherein said emulsion polymerization is conducted in the presence of water, a surfactant in amounts effective to emulsify the polymer in the water, a free-radical initiator, and from about 0.5 to about 20 weight percent of an alcohol selected from the group consisting of a $C_2$–$C_{12}$ linear or branched monohydric alcohol and a non-polymeric polyhydric alcohol, based on the total weight of said emulsion, wherein said emulsion polymerization is conducted in the absence of a polymeric colloidal stabilizer.

2. The composition of claim 1 wherein said emulsion comprises from about 15 to about 40 weight percent of said polymer, based on the total weight of said emulsion.

3. The composition of claim 1 wherein said emulsion comprises from about 0.1 to about 5 weight percent of said surfactant, based on the total weight of monomer, said surfactant selected from the group consisting of anionic, cationic, non ionic, amphoteric and zwitterionic surfactants.

4. The composition of claim 1 wherein the monomer (b) is selected from the group consisting of N,N-dimethylamino ethyl methacrylate, N,N-diethylamino ethyl acrylate, N,N-diethylamino ethyl methacrylate, N-t-butylamino ethyl acrylate, N-t-butylamino ethyl methacrylate, N,N-dimethylamino propyl acrylamide, N,N-dimethylamino propyl methacrylamide, N,N- diethylamino propyl acrylamide and N,N-diethylamino propyl methacrylamide.

5. A thickened aqueous composition having pH of less than or equal to 9, comprising: a stable emulsion of a polymer, said emulsion prepared by single-stage emulsion polymerization of monomers consisting of from about 5 to about 80 weight percent of an acrylate monomer (a) selected from the group consisting of a $C_2$–$C_6$ alkyl ester of acrylic acid and a $C_1$–$C_6$ alkyl ester of methacrylic acid, and from about 5 to about 80 weight percent of a monomer (b) selected from the group consisting of a vinyl-substituted heterocyclic compound containing at least one of a nitrogen or sulfur atom, (meth)acrylamide, a mono- or di- ($C_1$–$C_4$)alkylamino ($C_1$–$C_4$)alkyl (meth) acrylate, and a mono or di-($C_1$–$C_4$)alkylamino ($C_1$–$C_4$) alkyl (meth)acrylamide, wherein the percentage of monomers is based on 100 weight percent, wherein said emulsion polymerization is conducted in the presence of water, a first surfactant in amounts effective to emulsify the polymer in the water, a free-radical initiator and from about 0.5 to about 20 weight percent of an alcohol selected from the group consisting of a $C_2$–$C_{12}$ linear or branched monohydric alcohol and a non-polymeric polyhydric alcohol, based on the total weight of said emulsion, wherein said single-stage emulsion polymerization is conducted in the absence of a polymeric colloidal stabilizer.

6. The composition of claim 5 further comprising a second surfactant which is the same as or different from said first surfactant.

7. The composition of claim 6 wherein said second surfactant is selected from the group consisting of anionic and nonionic surfactants.

8. The composition of claim 5 wherein said emulsion comprises from about 15 to about 40 weight percent of said polymer, based on the total weight of said emulsion.

9. The composition of claim 5 wherein said emulsion comprises from about 0.1 to about 5 weight percent of said first surfactant, based on the total weight of monomer, said first surfactant selected from the group consisting of anionic, cationic, nonionic, amphoteric and zwitterionic surfactants.

* * * * *